United States Patent [19]
Schmidt et al.

[11] Patent Number: 5,714,156
[45] Date of Patent: Feb. 3, 1998

[54] ABSORBENT GELLING MATERIAL COMPRISING A DRY MIXTURE OF AT LEAST TWO TYPES OF HYDROGEL-FORMING PARTICLES AND METHOD FOR MAKING THE SAME

[75] Inventors: Mattias Schmidt, Idstein; Manfred Plischke, Steinbach/Ts., both of Germany; Stephen Allen Goldman, Wyoming, Ohio

[73] Assignee: The Procter & Gamble Company, Cincinnati, Ohio

[21] Appl. No.: 765,503

[22] PCT Filed: Jul. 3, 1995

[86] PCT No.: PCT/US95/08379

§ 371 Date: Jan. 6, 1997

§ 102(e) Date: Jan. 6, 1997

[87] PCT Pub. No.: WO96/01657

PCT Pub. Date: Jan. 25, 1996

[30] Foreign Application Priority Data

Jul. 5, 1994 [EP] European Pat. Off. .............. 94110451

[51] Int. Cl.⁶ .................................................. A61K 9/14
[52] U.S. Cl. ...................... 424/404; 424/484; 424/486; 424/487
[58] Field of Search ........................ 424/404, 484, 424/486, 487; 604/358, 365, 368, 367, 372, 378, 382

[56] References Cited

U.S. PATENT DOCUMENTS

| | | | |
|---|---|---|---|
| 4,333,464 | 6/1982 | Nakano | 128/290 R |
| 4,411,660 | 10/1983 | Dawn et al. | 604/396 |
| 4,902,544 | 2/1990 | Kim et al. | 428/36.1 |
| 5,505,718 | 4/1996 | Roe et al. | 604/368 |

FOREIGN PATENT DOCUMENTS

| | | |
|---|---|---|
| 0 278 601 A2 | 8/1988 | European Pat. Off. . |
| 0 304 319 B1 | 2/1989 | European Pat. Off. . |
| 0 401 189 B2 | 12/1990 | European Pat. Off. . |
| 0 407 838 A | 1/1991 | European Pat. Off. . |
| 1-544 002 | 4/1979 | United Kingdom . |
| 91/12029 | 8/1991 | WIPO . |

*Primary Examiner*—Thurman K. Page
*Assistant Examiner*—Kathryne E. Shelborne
*Attorney, Agent, or Firm*—Uwe T. Hirsch; Carl J. Roof; E. Kelly Linman

[57] ABSTRACT

The invention relates to an absorbent gelling material comprising a dry mixture of at least a first type of hydrogel-forming particles and a second type of hydrogel-forming particles. The absorbent gelling material in accordance with the invention is characterized in that the first type of hydrogel-forming particles has an Absorption Against Pressure value which is higher than the Absorption Against Pressure value of the second type of hydrogel-forming particles, the weight of the second type of hydrogel-forming particles forming at least 10% of the combined weight of the first and second type of hydrogel forming particles. The invention also relates to a method for making such material.

18 Claims, 6 Drawing Sheets

ABSORBENT GELLING MATERIAL COMPRISING A DRY MIXTURE OF AT LEAST TWO TYPES OF HYDROGEL-FORMING PARTICLES AND METHOD FOR MAKING THE SAME

This application is a 371 of PCT/US95/08379 filed Jul. 03, 1995.

FIELD OF THE INVENTION

The invention relates to an absorbent gelling material comprising a dry mixture of at least a first type of hydrogel-forming particles and a second type of hydrogel-forming particles. The invention also relates to a method for making such a material.

BACKGROUND OF THE INVENTION

Such absorbent gelling materials are described in many prior art references.

EP-A-0 407 838 discloses a gel-forming material for use in foodstuffs, which comprises a mixture of a crosslinked polymer and a non-crosslinked polymer for lump-free solution in water.

EP-A-0 278 601 discloses a mixture of an absorbent gelling polymer, such as formed from water-soluble, ethylenically unsaturated monomers or crosslinked products thereof, including acrylic acid or a salt of acrylic acid as the main component, and inorganic material such as aluminia, or silica. The polymers in the mixture may be comprised of any combination of two or more chemically different types. The disclosed absorbent mixture is suited to absorb both low-viscosity and high-viscosity liquids.

WO 91/12029 discloses an odor control composition comprising aggregated absorbent gelling material particles and zeolite material. The absorbent gelling material is made of hydrolized acrylonitrile grafted starch, acrylic acid grafted starch, polyacrylates, malice anhydride-based copolymers and combinations thereof.

U.S. Pat. No. 4,333,464 discloses a sanitary napkin having water absorbent polymer which may comprise a mixture of two types of absorbent gelling material from the group consisting of starch, β-hydroxyethylacrylate, acrylonitrile, acrylic acid and acrylamide, carboxymethylcellulose, hydrophilic copolymers of acrylates, copolymers of a vinyl ester and an ethylenically unsaturated carboxylic acid and their saponification products, polyvinyl alcohol, and its derivatives.

U.S. Pat. No. 4,902,544 discloses a flexible tubular casing comprising a crosslinked hydrocolloid and naturally occurring cellulose such as saw dust, crushed corncobs, cottonlinters, wood pulp and the like, ion-exchange resins or clay minerals.

GB-B-1 544 002 discloses a mixture of a salt of an acrylic acid polymer and either guar gum, alginates or xanthan gum to provide an absorbent material with good absorbent properties, irrespective of the presence of an electrolyte in the liquid to be absorbed. Polyvalent ions may be incorporated in the absorbent composite.

U.S. Pat. No. 4,411,660 discloses in an absorbent product two layers of absorbent material of different types, such that the upper layer gels slower than the first layer.

European Patent Specification EP-B-0 401 189 discloses that favourable properties of absorbent products can be achieved by using two different types of absorbent gelling material in separate layers, rather than as a mixture of the two absorbent gelling materials in a single layer.

Absorbent gelling materials are extensively used in absorbent hygiene articles such as diapers or sanitary napkins, due to their high absorption capacity for liquids, which may typically range from 15 g per gram to about 50 g/g. The gelling material is most often applied in particulate form in particle sizes ranging from 20 to 2000 micrometers. The particles that are used in absorbent hygiene articles can be mixed with hydrophilic fibers or can be employed in layers solely consisting of the hydrogel-forming particles.

An important parameter which describes the ability of the absorbent gelling material to take in liquids under in-use conditions, i.e. when applied in an absorbent product such as a baby diaper or a sanitary napkin, is the Absorption Against Pressure value, further referred to as the AAP-value, of the material. The absorbent gelling materials most useful in absorbent products have AAP-values of 15 g/g or higher at a confining pressure of 49.2 $gcm^{-2}$ (0.7 psi). Absorbent gelling materials having a relatively high AAP value, will show relatively little gel blocking and tend to maintain an open structure through which liquids can enter into the absorbent material. The acquisition properties of absorbent structures that contain relatively high concentrations of hydrogel-forming material and their ability to quickly absorb body fluids are mainly determined by the AAP value.

Another important parameter which describes the properties of the absorbent gelling material is the Teabag Centrifuge Capacity-value, further referred to as the TCC-value. The TCC-value is a measure of how much liquid, once it has been absorbed by the absorbent gelling material, is retained in the material. The amount of liquid travelling back from the core of an absorbent product in which the absorbent gelling material is incorporated toward a topsheet (so-called re-wet) is mainly determined by the TCC value. Generally, the absorbent gelling materials having higher AAP-values can only retain a limited amount of liquids. In existing absorbent gelling materials, it has not been possible to combine a sufficiently high AAP value and a desirably high TCC-value.

When a bulk mass of hydrogel-forming particles of a relatively low AAP-value is wetted under a confining pressure, the swollen particles tend to be deformed so as to substantially reduce or eliminate the interstices between particles. When this occurs, the rate at which liquid can be absorbed by the hydrogel-forming particles is substantially reduced. This phenomenon is often referred to as gel blocking. This situation is typically exacerbated when significant quantities of hydrogel-forming particles having an average dimension below 150 micrometers (the so-called "fines") are present. These fines will tend to flow into the interstices between the larger particles, and hence further reduce the liquid uptake rate. To avoid the adverse effect of fines, the fraction of fines present in the bulk of absorbent gelling material is often reduced, for instance by sieving. This has for instance been disclosed in EP-A-0 304 319 (Goldman), which discloses that improved liquid handling properties of absorbent structures containing hydrogel-forming particles are obtained by having a mass mean particle size greater than about 400 microns and minimizing the quantity of particles with a size less than about 200 microns.

In view of the above, it is an object of the present invention to provide an absorbent gelling material having relatively high Teabag Centrifuge Capacity values and relatively high Absorption Against Pressure values.

It is another object of the invention to provide an absorbent gelling material comprising at least two types of hydrogel-forming particles, wherein AAP-value of the combined hydrogel-forming materials is improved.

It is a further object of the invention to provide an absorbent gelling material which is relatively easy to manufacture and which is cost-effective.

It is again a further object of the invention to provide an absorbent gelling material which has a relatively high AAP-value and which comprises a relatively large amount of fines.

It is again another object of the present invention to provide a method of manufacturing an absorbent gelling material comprising at least two types of hydrogel-forming particles whereby the properties of the hydrogel-forming material can relatively easily be modified.

SUMMARY OF THE INVENTION

The absorbent gelling material in accordance with the invention is characterised in that the first type of hydrogel-forming particles has an Absorption Against Pressure value which is higher than the Absorption Against Pressure value of the second type of hydrogel-forming particles, the weight of the second type of hydrogel-forming particles forming at least 10% of the combined weight of the first and second type of hydrogel-forming particles.

When two types of hydrogel-forming material are mixed, preferably in their dry state, it has surprisingly been found that the impact of the type of hydrogel-forming particles having the higher AAP-value on the AAP-value of the mixture, is relatively high. It has been found that the mixture of two types of hydrogel-forming particles of different AAP-values has a higher AAP-value than could be expected on the basis of the weight fractions in the mixture of the two types of hydrogel-forming particles. Alternatively, it can be said that a "nonlinear mixing effect" is observed. For specific mixtures or combinations of hydrogel-forming particles it has also surprisingly been found that the AAP-value of the combined particles in the mixture is higher than the AAP-value of any of the individual components of the mixture. This will be called "synergistic effect".

It has been found that by addition of a relatively small amount of hydrogel-forming particles of high AAP-values to a hydrogel-forming-material of lower AAP-values and higher TCC-values, the AAP-value of the mixture can be increased without lowering the Teabag Centrifuge Capacity value to undesirable low values.

It has been found especially advantageous to improve the AAP-value of a pre-determined type of hydrogel-forming material by addition of a fraction of a different type of hydrogel-forming particles of higher AAP-value and smaller mass median particle size. Without wishing to be bound by any theory, it is believed that particles having a higher AAP-value have a larger resistance to deformation upon absorption of liquids than the "softer" particles of lower AAP-values. In the mixture, the smaller, "harder" particles maintain an open structure and prevent the "softer", larger particles from forming an impermeable barrier upon swelling. In this way, a synergistic effect on the AAP-value of the mixture might be explained.

While the AAP value of the mixture increases in a non-linear manner upon addition of a specific fraction of particles of higher AAP-value, the decrease in the TCC-value of the mixture caused by this addition is linear. The mixture will have an AAP-value which is higher than would be expected on the basis of the weight fraction of the hydrogel-forming particles of a higher AAP-value in the mixture, and will have a TCC-value which is proportional to the weight fraction of the hydrogel-forming particles having the higher AAP-value. As relatively little hydrogel-forming particles of a high AAP-value need to be added to the mixture to increase the mixture's AAP-value to a predetermined value the corresponding reduction in TCC-value of the mixture is minimized.

By a "type" of hydrogel-forming particles is meant a group of hydrogel-forming particles having a predetermined AAP-value. Within one type, the particles may be of identical or different size. For instance, in one mixture according to the invention the size of the particles of the first and second type may each have a predetermined particle size distribution.

The mass median particle size and the shape of the particle size distribution for the first and the second type of material may be similar. In such a case, differences in AAP and/or TCC values between the two types of hydrogel-forming particles can arise from e.g., differences in chemical composition or the degree of surface crosslinking. The mixture has the same particle size distribution as each of its components. Alternatively, the particle size distributions of each of the components of the mixture may be different, such that the mixture has a bi-modal (or higher modal if more components are comprised in the mixture) particle size distribution.

Again, alternatively, the mixture may comprise a single bulk material, comprising a fraction which has been chemically modified prior to mixing, for instance by surface crosslinking.

The shape of the particles comprised in each type in the mixture may be similar for both types or may differ for each type and may comprise spheres, fibers, flakes, rods, irregularly shaped particles, agglomerates and other particle shapes.

Hydrogel-forming particles of different types have different AAP-values. In an embodiment of the absorbent gelling material according to the invention, the difference between the AAP-values of the first and the second type of hydrogel-forming particles is at least 2 g/g.

The word "dry mixture" is intended to mean a combination of at least two individual amounts of hydrogel-forming particles, the amounts having mutually different AAP- or TCC-values, the particles maintaining their physical identity. A homogeneous bulk material comprising only particles of identical chemical composition and identical degrees of surface crosslinking, is not considered to form a mixture in the sense of the absorbent material according to the invention.

In the mixture, the particles of the first type of material can be agglomerated with the particles of the second type of material, or may be otherwise mutually connected. The mixture may be in the form of a free-flowing powder or may comprise particles which are mutually connected to form a macrostructure. Such aggregated macro-structures are described in U.S. Pat. Nos. 5,102,597 (Roe) and 5,124,188 (Roe). The word "dry" is not intended to mean the complete absence of water from the mixture. Hydrogel-forming particles will pick up moisture from the ambient during production and storage. With "dry" is meant that the mixture maintains its particulate character and is not substantially gelled. Moisture contents less than about 20 percent, preferably less than about 5 percent by weight are intended to be comprised in the absorbent materials according to the invention.

In one embodiment of an absorbent gelling material according to the invention, the second type of hydrogel-forming particles, having the lower AAP-value, has a mass median particle size not substantially smaller than the mass median particle size of the first type of hydrogel-forming particles having the higher AAP-value.

It has been observed that the above-described synergistic effects are reduced when in a mixture the smaller particles have the lower AAP-value. A possible explanation for this might be that when the smaller particles have an AAP-value which is lower than the AAP value of the larger particles, the smaller particles have a reduced capability to press the larger particles aside upon swelling of the smaller particles and to maintain a liquid-permeable structure of larger particles. Also, the smaller particles of lower AAP value will tend to deform more easily and can flow into (and deform within) the interstices of the larger particles, resulting in increased gel blocking.

Another embodiment of an absorbent material according to the invention is characterised in that the first type of hydrogel-forming particles have a TCC-value which is greater than the value of the second type of hydrogel-forming particles, the amount of the second type of hydrogel-forming particles forming at least 10% of the combined weight of the first and second type of hydrogel-forming-materials, the Absorption Agains Pressure value of the mixture being higher than the Absorption Against Pressure value of either one of the first type of hydrogel-forming particles and the second type of hydrogel-forming particles, wherein the absorption against pressure values are measured at pressures between 21.1 gcm$^{-2}$ (0.3 psi) and 70.3 gcm$^{-2}$ (1 psi), preferably between 35.2 gcm$^{-2}$ (0.5 psi) and 56.2 gcm$^{-2}$ (0.8 psi).

A method of manufacturing an absorbent gelling material according to the invention comprises mixing of two particulate hydrogel-forming materials of different AAP- and/or TCC-values.

A preferred method of manufacturing an absorbent gelling material according to the invention comprises the steps of separating a weight fraction of hydrogel-forming particles from a homogeneous bulk material, physically or chemically treating the separated fraction and mixing the treated fraction back into the main fraction to form the mixture according to the invention. The homogeneous bulk material may have been produced by any known method and may be surface-crosslinked or homogeneously crosslinked.

The separated fraction can comprise for instance the tail of a particle size distribution comprising particles of a relatively small particle size, and undergoes a surface crosslinking step to increase the AAP-value of the fraction. By selectively treating a fraction of the homogenous mixture, the AAP-value of the separated fraction can be improved. The effect of the improvement of the AAP-value of the fraction on the AAP-value of the mixture of the combined particles is large. It has been found that by only treating a specific fraction of the bulk material, rather than treating all of the bulk material, a surprisingly high overall AAP is achieved without negatively affecting the Teabag Centrifuge Capacity values.

Surface crosslinked hydrogel-forming absorbent polymers have a higher level of crosslinking in the vicinity of the surface than in the interior. As used herein, "surface" describes the outer-facing boundaries of the particle, fiber, etc. For porous hydrogel-forming absorbent polymers (e.g., porous particles, etc.), exposed internal boundaries can also be included. By a higher level of crosslinking at the surface, it is meant that the level of functional crosslinks for the hydrogel-forming absorbent polymer in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given hydrogel-forming absorbent polymer. For particulate hydrogel-forming absorbent polymers, surface crosslinking can vary with particle size, porosity, etc. Depending on variations in surface:volume ratio within the hydrogel-forming absorbent polymer (e.g., between small and large particles), it is not unusual for the overall level of crosslinking to vary within the material (e.g., be greater for smaller particles).

Surface crosslinking is generally accomplished after the final boundaries of the hydrogel-forming absorbent polymer are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel-forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.)

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application W092/16565 (Stanley), published Oct. 1, 1992, published PCT application W090/08789 (Tai), published Aug. 9, 1990; published PCT application W093/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No.

4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference.

Alternatively, the method according to the invention comprises the steps of polymerising a first monomer forming the first type of hydrogel-forming particles polymerising a second monomer forming the second type of hydrogel-forming particles, and mixing the first type and second type of hydrogel-forming particles.

The advantage of this method is that it can easily be carried out using existing manufacturing equipment. In the known processes of manufacturing hydrogel-forming particles of a single type, the precursor materials are often reacted in a number of separate reaction vessels for reasons of homogeneity and control of the reaction mixture. After formation of the absorbent polymer material from the precursor materials, the polymer material from each reaction vessel is dried and ground to the desired particle size. Then, the particles formed in the different vessels are mixed and further treated, for instance by surface cross-linking to obtain a bulk material. When in the described process different precursor materials are used in each of the reaction vessels, an absorbent material according to the invention can be easily obtained.

BRIEF DESCRIPTION OF THE DRAWINGS

The invention will be described in detail with reference to the accompanying drawings. In the drawings FIGS. 2a, 2b–4a, 4b show AAP and TCC values for mixtures of different weight percentages of hydrogel-forming-materials.

DETAILED DESCRIPTION OF THE INVENTION

Hydrogel Forming Absorbent Polymers

The hydrogel-forming absorbent polymers useful in the present invention include a variety of substantially water-insoluble, but water-swellable polymers capable of absorbing large quantities of liquids. Such polymers materials are also commonly referred to as "hydrocolloids", or "superabsorbent" materials. These hydrogel-forming absorbent polymers preferrably have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups and quaternary ammonium salt groups. These, non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, mothacrylic acid, ethacrylic acid, -chloroacrylic acid, a-cyanoacrylic acid, -methylacrylic acid (crotonic acid), -phenylacrylic acid, -acryloxypropionic acid, sorbic acid, -chlorosorbic acid, angelic acid, cinnamic acid, p-chlorocinnamic acid, -sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and mothacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making hydrogel-forming particles are slightly network crosslinked polymers of partially neutralized polyacrylic acids and starch derivatives thereof. Most preferably, the hydrogel-forming particles comprise from about 50 to about 95%, preferably about 75%, neutralized, slightly network crosslinked, polyacrylic acid (i.e. poly (sodium acrylate/ acrylic acid)).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures.

Processes for network crosslinking the polymers and typical network crosslinking agents are described in greater detail in the hereinbefore-referenced U.S. Pat. No. 4,076,663, and in DE-A-4020780 (Dabmen).

Although the hydrogel-forming absorbent polymers can have a size varying over a wide range, specific particle size distributions and sizes are preferred. For purposes of the present invention, particle size is defined for hydrogel-forming absorbent polymers that do not have a large greatest dimension/smallest dimension ratio such as fibers (e.g., granules, flakes, or pulverulents) as the dimension of a precursor particle that is determined by sieve size analysis. Thus, for example, a hydrogel-forming absorbent polymer particle that is retained on a standard #30 sieve with 600 micron openings is considered to have a particle size greater than 600 microns, a hydrogel-forming absorbent polymer particle that passes through the #30 sieve with 600 micron openings and is retained on a standard #35 sieve with 500 micron openings is considered to have a particle size between 500 and 600 microns, and a hydrogel-forming absorbent polymer particle that passes through a #35 sieve with 500 micron openings is considered to have a particle size less than 500 microns. For preferred hydrogel-forming absorbent polymers useful in the present invention, the particles will generally range in size from about 1 micron to about 2000 microns, more preferably from about 20 microns to about 1000 microns.

Further, for purposes of this invention, the mass median particle size of the hydrogel-forming absorbent polymers is important in determining the characteristics and properties of the resultant particles. The mass median particle size of a given sample of hydrogel-forming absorbent polymer particles is defined as the particle size that divides a sample in half on a mass basis. Instead of the mass median particle size, the mass average particle size could be specified as a measure for the dimension of the particles, wherein the mass average particle size is the average particle size of the sample on a mass basis. A method for determining the mass median particle size of a sample is described hereinafter in the Test Methods section. The mass median particle size of the hydrogel-forming absorbent polymer particles will generally be from about 20 microns to about 1500 microns, more preferably from about 50 microns to about 1000 microns. For preferred hydrogel-forming absorbent polymers useful in the present invention, the particles have a mass median particle size less than about 1000 microns, more preferably less than about 600 microns, most preferably less than about 500 microns.

The particle size of materials having a large greatest dimension/smallest dimension such as fibers is typically defined by their largest dimension. For example, if hydrogel-forming absorbent polymeric fibers are used in the present invention, the length of the fibers is used to define the "particle size." (The denier and/or the diameter of the fibers can also be specified.) For exemplary embodiments of hydrogel-forming absorbent polymers useful in the present invention, the fibers have a length greater than about 5 mm, preferably between about 10 mm and about 100 mm, more preferably between about 10 mm and about 50 mm.

Preferred hydrogel-forming absorbent polymer particles of the present invention are those which exhibit a high absorptive capacity or Teabag Centrifuge Capacity value. Absorptive capacity, or Teabag Centrifuge Capacity, refers to the capacity of a given polymer to absorb liquids with which it comes into contact under free-swelling conditions. TCC can vary significantly with the nature of the liquid being absorbed and with the manner in which the liquid contacts the polymer material. For purposes of the present invention, Teabag Centrifuge Capacity is defined in terms of the amount of 0.9% saline solution absorbed by any given polymer in terms of grams of saline solution per gram of polymer material in a Tea bag Centrifuge Capacity test procedure hereinafter defined in the Test Methods section. Preferred hydrogel-forming absorbent polymer particles of the present invention are those which have Teabag Centrifuge Capacity values of at least about 20 grams, more preferably at least about 25 grams, of saline solution per gram of polymer material. Typically, the hydrogel-forming absorbent polymer particles useful herein have Teabag Centrifuge Capacity values of from about 20 grams to about 70 grams {Note inconsistency with 40/50 value used earlier} of saline solution per gram of polymer. Mixtures of hydrogel-forming absorbent polymers particles having this relatively high absorptive capacity characteristic are especially useful in the present invention since the resultant absorbent member formed from such particles can, by definition, hold desirably high amounts of discharged body exudates such as urine.

While all of the particles of the component of the mixture can be formed from the same hydrogel-forming absorbent polymer with the different Absorption Against Pressure and/or Teabag Centrifuge Capacity properties, this need not be the case. For example, some particles can comprise a starch-acrylic acid graft copolymer while other particles can comprise a slightly network crosslinked polymer of partially neutralized polyacrylic acid. Further, the particles can vary in size, or shape. For preferred hydrogel-forming absorbent polymers useful in the present invention, the particles consist essentially of slightly network crosslinked polymers of partially neutralized polyacrylic acid.

Absorbent Articles

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Figure 1:
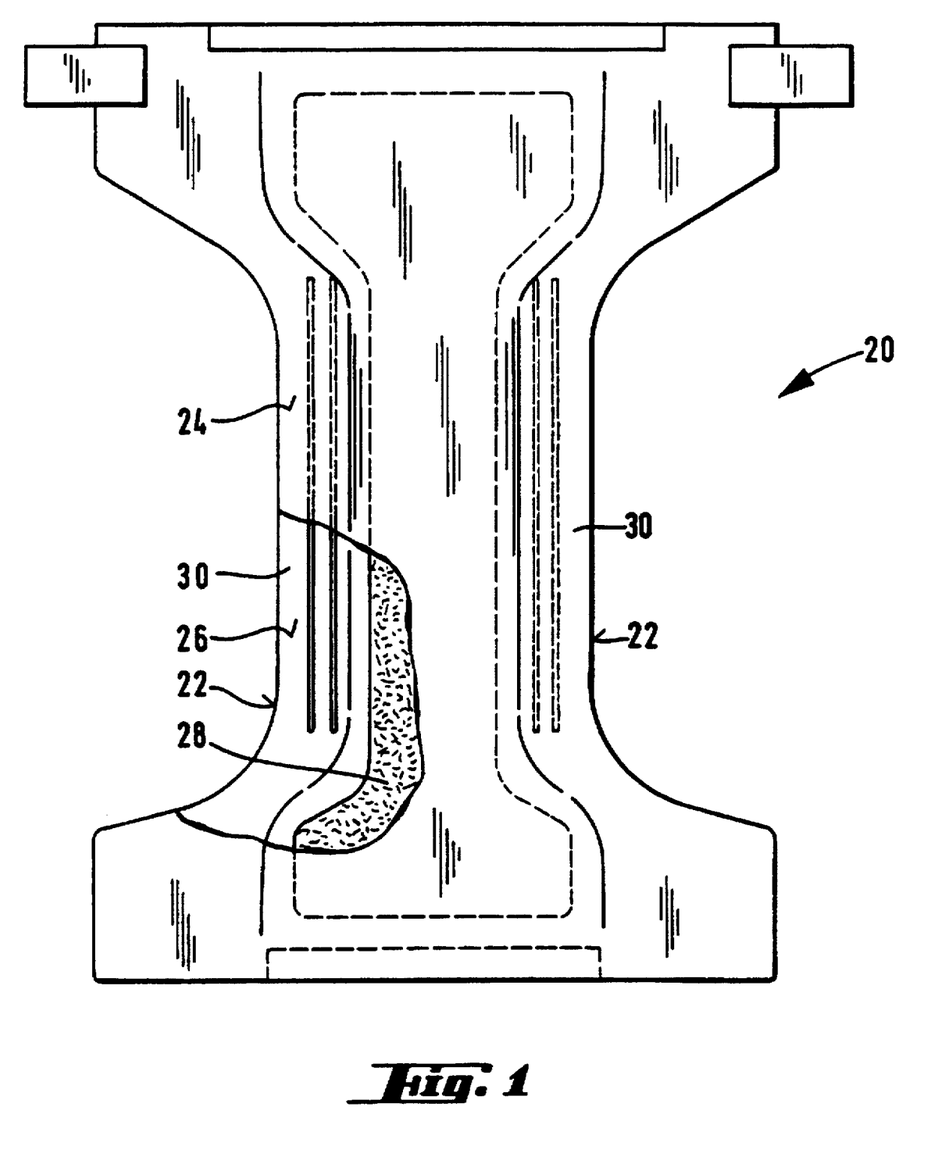
FIG. 1 shows a plan view of an absorbent article according to the invention in its flattened state.

FIG. 1 is a plan view of the diaper 20 in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26; elasticised side panels 30.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 22 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. A preferred embodiment of the absorbent core 28 comprises the absorbent gelling material according to the invention. For cores of relatively low caliper such as smaller than 4 mm and concentrations of hydrogel-forming particles of more than 30% by weight, particularly from 50% up to 100% by weight, it is desirable that the AAP-values measured at a pressure of 49.2 g/cm$^{-2}$ (0.7 psi) are at least 20 g/g. As these cores comprise relatively little space in the direction of their thickness, they need to be able to rapidly absorb the liquid into the available hydrogel-forming material, in order to prevent pooling of the liquid on the topsheet or run off of the liquid from the topsheet.

For such cores, the absorbent gelling material according to the invention can be tailored to have a higher percentage (above 50%) of hydrogel-forming particles of higher AAP-values.

By mixing of two types of hydrogel-forming particles having mutually different AAP-values or different TCC-values, a large freedom in design of the absorbent gelling material can be achieved and the properties of the absorbent gelling material can be tailored to meet the specific needs of the type of absorbent core in which they are incorporated. For instance, the absorbent gelling materials according to the invention can be used in cores comprising a lower layer of absorbent gelling material having an AAP-value of at least 15 g/g at 49.2 gcm$^{-2}$ (0.7 psi). Such cores are described in European Patent Application No.'s 93305150.0 and 93309614.1.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H.B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbonded, carded, wetlaid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

Test Methods

Absorption Against Pressure Test

This test measures the absorptive capacity of a superabsorbent material absorbing against an external pressure of between 21.1 gcm$^{-2}$ (0.3 psi) and 70.3 gcm$^{-2}$ (1 psi), in terms of the uniaxial swelling of the superabsorbent material against that pressure. For absorbent gelling material mixtures of two or more types of hydrogel-forming particles, it is observed that the Absorption Against Pressure curve, with varying percentages of the components of the mixture, strongly depends on the pressure conditions. For an accurate reflection of in-use conditions, the pressure at which the AAP-values should be measured is between 21.1 g/cm$^2$ (0.3 psi) and 70.3 g/cm$^2$ (1 psi). The AAP-value reflects the gel stiffness of an absorbent material. Absorbent particles which maintain a particulate structure when wet (i.e., maintain interstitial voids), will show a good absorption of liquids and do not collapse into an impermeable gel mass. Hydrogel-forming materials of low AAP-values, will tend to form a weak gel which is relatively impermeable to liquids and which collapses under pressure.

A ceramic filter plate having a diameter of 120 mm and a porosity of "Zero"(ceramic filter Duran from Schott) is placed in a petridsh having a diameter of 150 mm and a height of 30 min. 0.9% by weight sodium chloride solution in distilled water is added to the Petri dish so that the filter plate is covered. A round filter paper having a diameter of 125 mm (Schwarzband 589 from Schleicher and Schull) is placed on the filter plate and is thoroughly wetted with the sodium chloride solution.

A Plexiglass cylinder having an inner diameter of 60 mm+/–0.1 mm and a height of 50 mm, is closed at its bottom with a screen filter cloth having apertures of a diameter of 36 μm (400 mesh). 0.9000 g+/–0.0005 g of superabsorbent material is carefully scattered onto the filter screen of a clean and dry Plexiglass cylinder, as described. It is necessary to obtain a homogeneous distribution of superabsorbent material on the mesh.

A cover plate having an outer diameter of 59 mm+/–0.1 mm, an inner diameter of 51 mm and the height of 25 mm, having an attached weight having a diameter of 50 mm and a height of 34 mm, has a weight which that correspond to a pre-determined pressure in the range between 20.1 g/cm$^2$ and 70.3 g/cm$^2$. The cover plate and weights are placed in the cylinder and the complete cylinder apparatus is weighed on a balance to the nearest 0.01 g. The complete cylinder apparatus is then placed on the wetted filter paper in the Petri dish, and is allowed to absorb for 1 hour. The cylinder apparatus is then removed from the filter plate and is re-weighed.

The cylinder apparatus and filter plate should be cleaned thoroughly between measurements, and the sodium chloride solution and filter paper should be renewed after each measurement.

The absorption against pressure (AAP is calculated as follows:

$$AAP = [(\text{weight of cyliner apparatus after absorption}) - (\text{weight of cylinder apparatus when dry})]:(\text{initial weight of superabsorbent material}).$$

Teabag Centrifuge Capacity Test

The Teabag Centrifuge Capacity test measures the Teabag Centrifuge Capacity values, which are a measure of the retention of liquids in the gelling material at hydrostatic pressure The superabsorbent material is placed within a "teabag", immersed in a 0.9% by weight sodium chloride solution for 20 minutes, and then centrifuged for 3 minutes. The ratio of the retained liquid weight to the initial weight of the dry superabsorbent material is the absorptive capacity of the superabsorbent material.

2 l of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from a company called Teekanne in Düsseldorf, Germany. The pouch is heat sealable with a standard kitchen plastic bag sealing device (e.g. VACUPACK$_2$ PLUS from Krups, Germany).

The teabag is opened by carefully cutting it partially, and is then weighed. A 0.200 g+/–0.005 g sample of the superabsorbent material is placed in the teabag. The teabag is then closed with a heat sealer. This is called the sample teabag.

An empty teabag is sealed and used as a blank.

Each teabag is then held horizontally, and the sample teabag is shaken so as to distribute the superabsorbent material evenly throughout the bag. The sample teabag and the blank teabag are then laid on the surface of the saline solution, and submerged for about 5 seconds using a spatular to allow complete wetting (the teabags will float on the surface of the saline solution but are completely wetted). The timer is started immediately.

After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of superabsorbent hydrogel-forming material is calculated as follows:

TCC = [(sample teabag weight after centrifuging) −

(blank teabag weight after centrifuging) −

(dry superabsorbent hydrogel-forming materal weight)] ÷

(dry superabsorbent material weight).

Mass median particle size determination

The particle size distribution of superabsorbent material is determined by placing a known weight of a sample in a Retsch mechanical sieving device, and shaking for a specified period of time under defined conditions. Sample sections that are retained on each sieve and the bottom pan are weighed and reported as percentages of the original sample weight.

100 g+/−0.5 g of dry superabsorbent polymeric material is weighed into a sample sup which is then closed by a lid.

Four sieves are nested from bottom to top as follows: stainless steel bottom pan, No. 325, No. 100, No. 50 and No. 20; these being numbers of the U.S. sieve series (ASTM-E-11-61). The sample is transferred to the upper most of the series of sieves, and the powder is distributed evenly around the screen. A stainless steel cover is places on the No. 20 sieve.

The nested sieves are placed in position on a Retsch testing sieve shaker Vibotronic Type VE1 with timer. It is ensured that the Retsch lid fits as tightly as possible against the top of the shaker. The timer is set for 10 minutes, and started to begin the test. When the shaker has stopped, the nest of sieves is removed from the shaker.

Each of the sieve fractions retained by the sieve is then weighed, for example by different measurements, to the nearest 0.0 g.

It is important to work quickly in this test to avoid moisture pickup by the superabsorbent material.

The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et. al), issued Oct. 29, 1991, which is incorporated by reference.

EXAMPLES

In the following examples, mixtures comprising different weight percentages of two types of hydrogel-forming particles were prepared by adding representative samples of each type of material in a test-tube to give a total amount of 10 g. The test-tube was shaken for 1 minute to mix the hydrogel-forming particles. The AAP-values and the TCC values of the mixtures were measured as described above, at a confining pressure of 49.2 g/cm$^2$ (0.7 psi). The confining pressure prevailing under in-use conditions of an absorbent article will vary depending on the size of users, the type of use, and usage conditions and typically can range from 21.1 g/cm$^2$ to 70.3 g/cm$^2$. The pressure of 49.2 g/cm$^2$ is a reasonable pressure for simulating typical in-use conditions for diapers of babies of between 9 and 25 kg.

In the test the following particulate hydrogel-forming materials were used:

SXM 50, a surface-crosslinked polyacrylate as produced by Chemische Fabrik Stockhausen GmbH, Postfach 570, 47705 Krefeld, Germany under the tradename "FAVOR SX". The mass median particle size of the SXM 50 material is 450 μm;

W52521, a polyacrylate absorbent gelling material produced by Stockhausen of mass median particle size of 460 μm; and W52859, a polyacrylate absorbent gelling material produced by Stockhausen of mass median particle size of 480 μm.

EXAMPLE I

In this example, the effect is measured of mixing two hydrogel-forming-materials having a similar mass median particle size and particle size distribution.

Figure 2A:
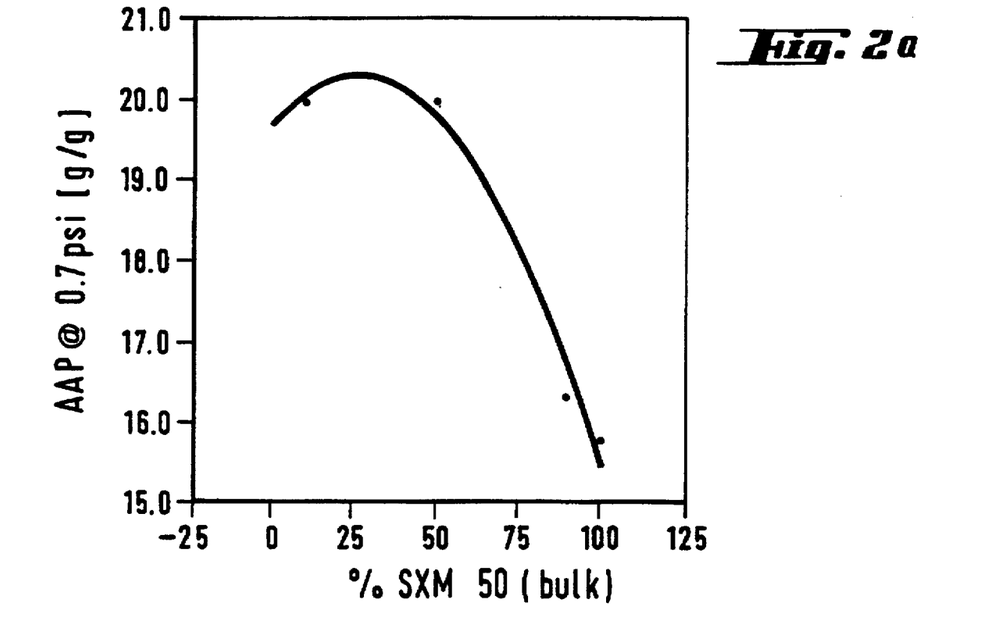
Figure 2B:
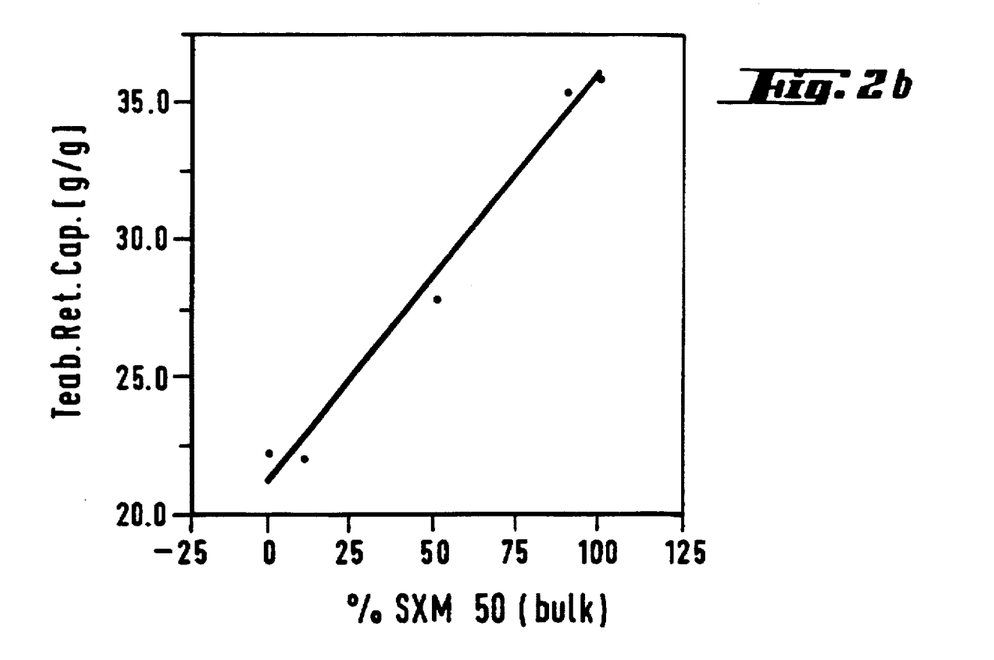

Bulk SXM 50 material was mixed with bulk W52521 material without a prior sieving step. The AAP-values and TCC values are indicated in table I. The results are presented graphically in FIG. 2.

TABLE I

Mixing of bulk SXM 50 (mass median particle size 450 μm) and bulk W52521 (mass median particle size 460 μm)

| % SXM 50 | % W 52521 | AAP (g/g) at 49.2 gcm$^{-2}$ | TCC (g/g) |
|---|---|---|---|
| 0 | 100 | 19.7 | 22.4 |
| 10 | 90 | 20.0 | 22.2 |
| 50 | 50 | 20.0 | 27.9 |
| 90 | 10 | 16.4 | 35.4 |
| 100 | 0 | 15.8 | 36.0 |

From FIG. 2 it is clear that at weight percentages of at least 50% of the W52521 material, the AAP value has a sustained value of about 20 g/g, the TCC-value of the mixture being between 22 g/g and 28 g/g. Therefore, the TCC-value of the W52521 material can be improved by adding up to 50% by weight of SXM50-material, without negatively affecting the AAP-value. Conversely, the AAP-value of the SXM50-material is improved by addition of at least 50% by weight of W52521 material.

EXAMPLE II

In this example the effect is measured of mixing relatively small particles having a high AAP value with relatively large particles having a low AAP value.

The smaller particles are obtained by sieving of the W 52521 bulk material through a standard #50 mesh sieve, and collecting the particles going through the sieve. The mass median particle size of the small particles was 190 μm. The larger particles were obtained by a sieving step using the same standard sieve, using the SXM 50 bulk material and collecting the particles remaining on the sieve. The mass median particle size of the large particles was 570 μm.

Figure 3A:
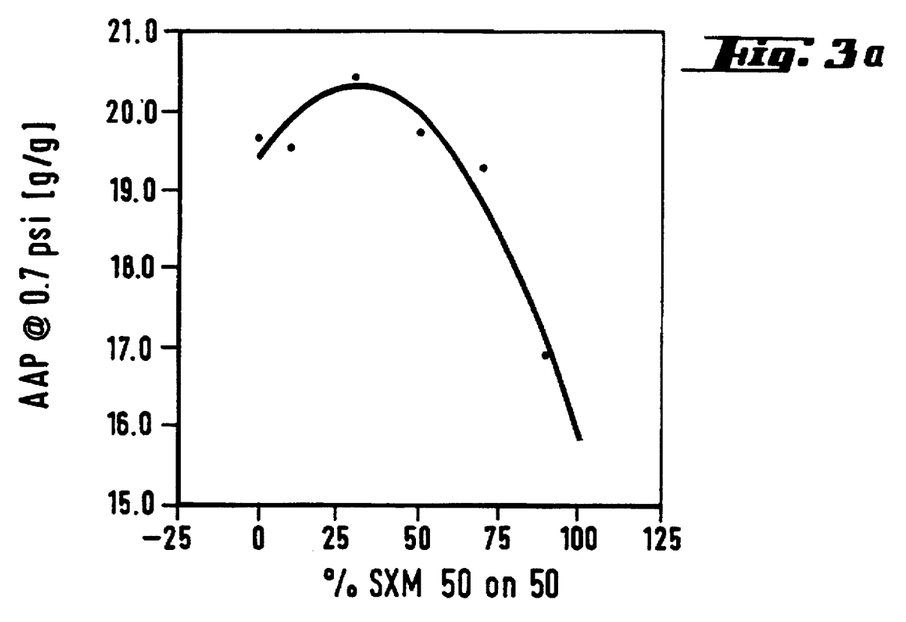
Figure 3B:
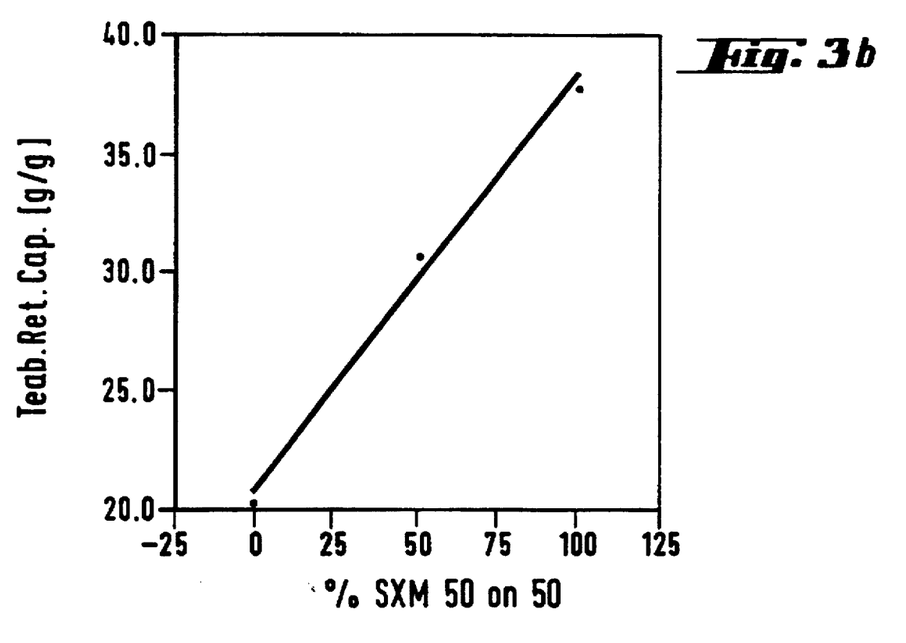

The AAP-values and TCC values are indicated in table II. The results are presented graphically in FIG. 3.

TABLE II

Mixing of SXM 50 on #50 mesh sieve (mass median particle size: 570 μm) and W52521 through #50 mesh sieve (mass median particle size 190 μm).

| % SXM 50 on # 50 | % W52521 through # 50 | AAP (g/g) at 49.2 g/cm² | TCC (g/g) |
|---|---|---|---|
| 0 | 100 | 19.7 | 20.3 |
| 10 | 90 | 19.6 | |
| 30 | 70 | 20.4 | |
| 50 | 50 | 19.7 | 30.7 |
| 70 | 30 | 19.3 | |
| 90 | 10 | 16.9 | |
| 100 | 0 | 15.9 | 37.8 |

From FIG. 3 it is clear that the maximum AAP value of about 20.4 g/g is reached for a percentage of about 70% by weight of the smaller W52521 particles, the TCC value being about 26 g/g.

Example III

In this example the effect is measured of mixing relatively small particles having a low AAP value with relatively large particles having a high AAP value.

The smaller particles are obtained by sieving of the SXM 50 bulk material through a standard #50 mesh sieve, and collecting the particles that pass through the sieve. The mass median particle size of the smaller particles was 190 μm. The larger particles were obtained by a sieveing step using the same standard sieve, using the W52521 bulk material and collecting the particles remaining on the sieve. The mass media particle size of the larger particles was 570 μm.

Figure 4A:
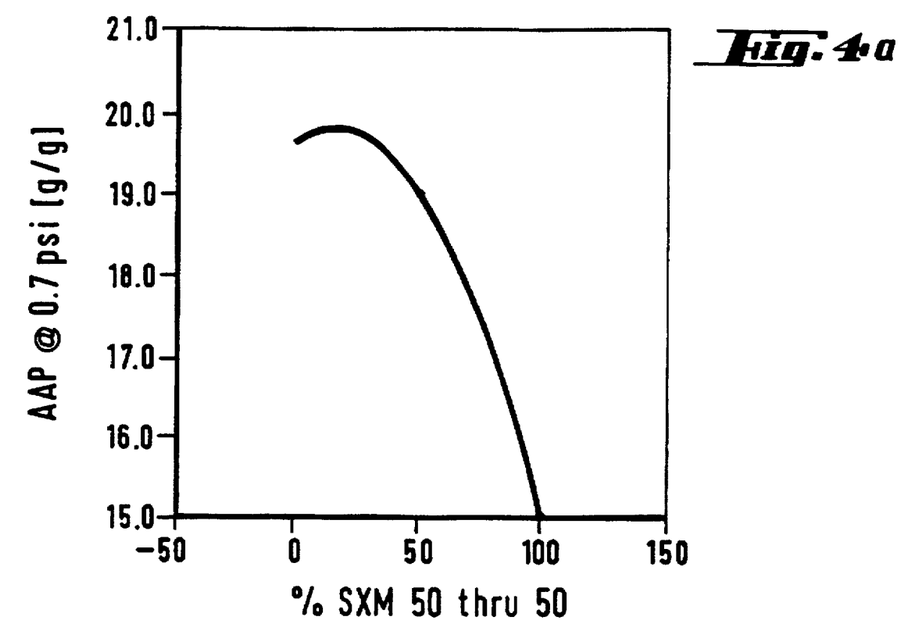
Figure 4B:
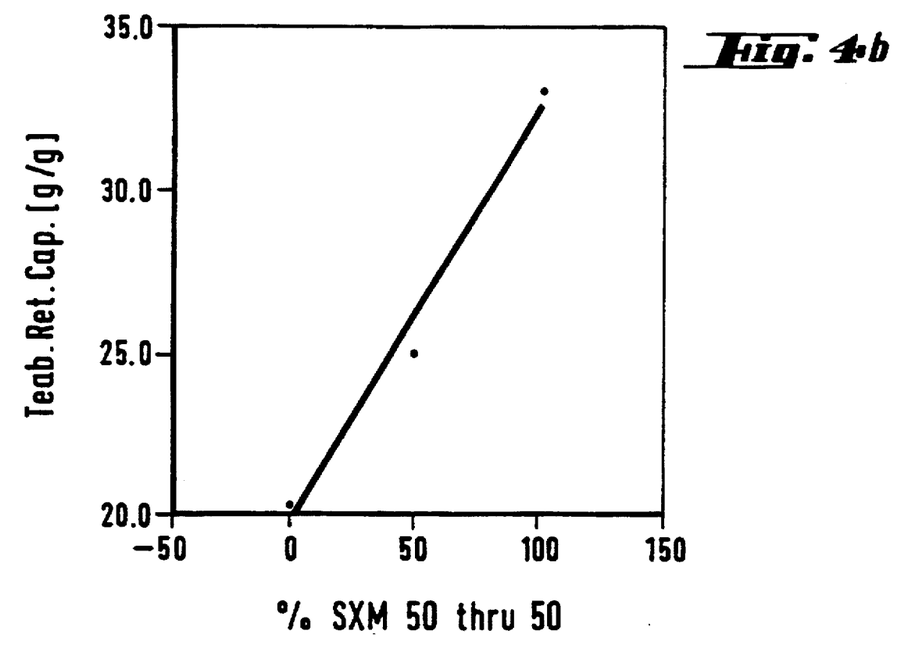

The AAP-values and TCC values are indicated in table III. The results are presented graphically in FIG. 4.

TABLE III

Mixing of SXM 50 through #50 mesh sieve (mass median particle size 190 μm) and W52521 on #50 mesh sieve (mass median particle size 570 μm)

| % SXM 50 through # 50 | % W52521 an # 50 | AAP (g/g) of 49.2 g/cm² | TCC (g/g) |
|---|---|---|---|
| 0 | 100 | 19.7 | 20.3 |
| 50 | 50 | 19.1 | 25.1 |
| 100 | 0 | 15.1 | 33.2 |

From FIG. 4 it is clear that synergystic effect of mixing smaller particles of lower AAP-values with larger particles of higher AAP-values is less pronounced than in example II. At concentrations of about 25% of the smaller particles, the AAP value is about 19.9 g/g, the TCC value being about 24 g/g.

Example IV

In this example the effect is measured of mixing two types of hydrogel-forming particles having a substantially similar AAP value, but differing in TCC-value. In this example bulk W52859 material having a mass median particle size of 480 μm was mixed with bulk W52521 material of mass median particle size of 460 μm.

Figure 5:
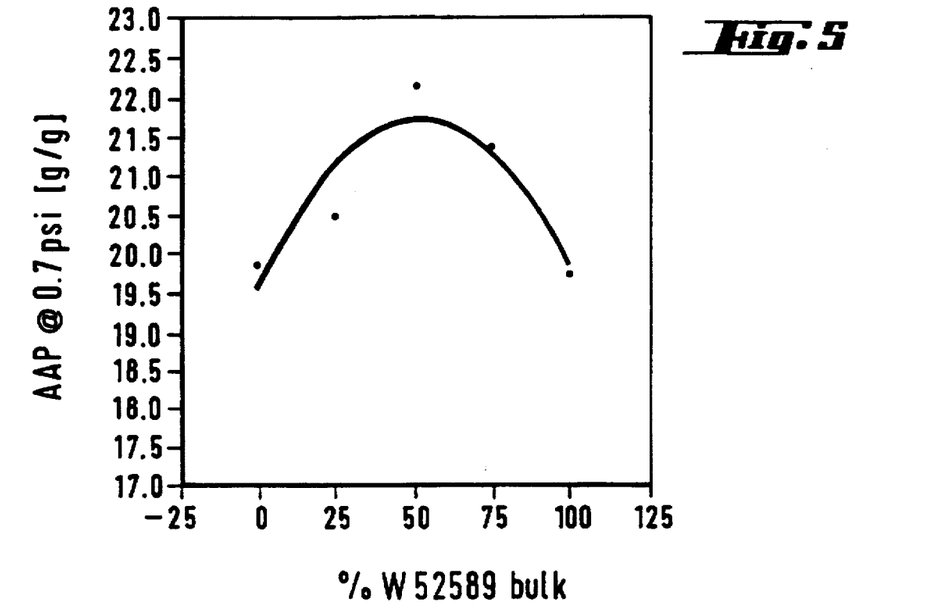
FIG. 5 shows the AAP value of a mixture of two types of hydrogel-forming particles having substantially similar AAP-values, FIG. 6 schematically shows the pressure dependence of the AAP-values, and FIGS. 7 and 8 schematically show a method of manufacturing an absorbent gelling material according to the invention.

The AAP and TCC values are indicated in Table IV. The results are presented graphically in FIG. 5.

TABLE IV

Mixing of bulk W52859 (mass median particle size 480 μm) and bulk W52521 (mass median particle size 460 μm)

| % W52859 bulk | % W52521 bulk | AAP (g/g) of 49.2 g/cm² | Teabag Centrifuge Capacity (g/g) |
|---|---|---|---|
| 0 | 100 | 19.9 | 20.6 |
| 25 | 75 | 20.5 | |
| 50 | 50 | 22.2 | |
| 75 | 25 | 21.4 | |
| 100 | 0 | 19.8 | 28 |

By selectively mixing about equal weights of hydrogel-forming materials of similar AAP-values but different Teabag Centrifuge Capacity values, a surprisingly high AAP-value is obtained which is higher than the AAP values of any of the constituent components.

Further examples of mixtures of absorbent gelling materials, according to the invention can be obtained by mixing of the following particulate hydrogel-forming materials:

SAB990 of mass median particle size of 570 μm with SXM100 of mass median particle size of 190 μm at a confining pressure of 21.1 gcm⁻². The SAB990 and the SXM100 materials are available from Stockhausen.

IM1000 and W52521 bulk material at a confining pressure of 21.1 gcm⁻². The IM1000 material is a starch grafted polyacrylate produced by Hoechst AG, Frankfurt am Main, Germany.

Without wishing to be bound by any particular theory, the discovered mixing effects can be understood by looking at the general pressure dependence of the AAP values and at the mechanism that controls the fluid uptake in the AAP test.

Figure 6:
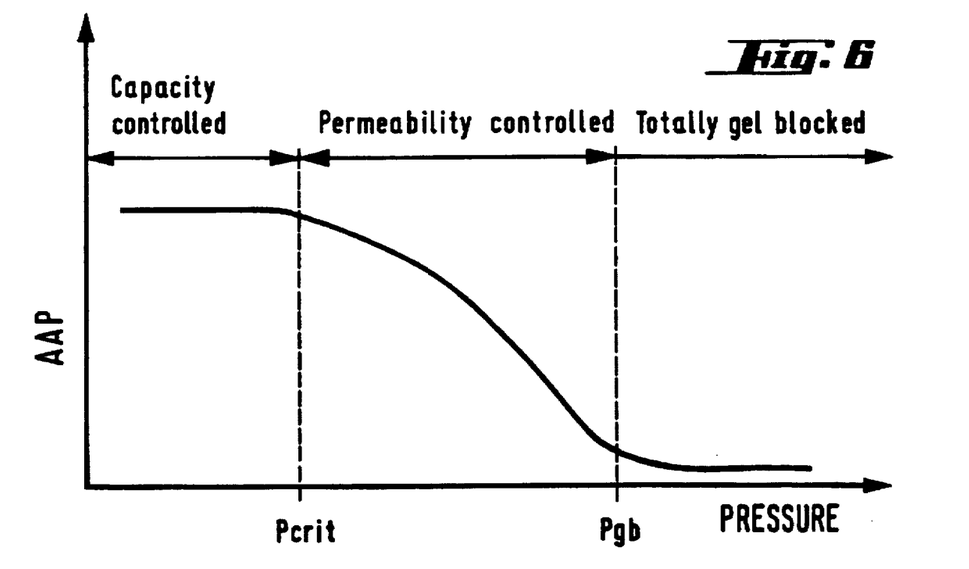

FIG. 6 shows the principal dependence of the AAP value of a given hydrogel-forming material on the confining pressure. The curve shows two characteristic pressures Pcrit and Pgb which determine the fluid uptake mechanism. For confining pressures less than the critical pressure Pcrit, the hydrogel-forming layer is very permeable and the fluid uptake is not hindered by gel blocking. As indicated in FIG. 6, the AAP-values in this pressure range are 'capacity cortrolled'. The hydrogel-forming layer can therefore swell to almost it's maximum capacity for that pressure. While AAP-values in this regime can still be impacted by pressure as a result of variation in hydrogel capacity and porosity, the changes with pressure tend to be relatively smaller.

For larger pressures, the fluid uptake is reduced, since the hydrogel-forming particles deform thus creating a less permeable layer through which fluid uptake is hindered. The hydrogel-forming material cannot achieve it's maximum capacity under these conditions. As indicated in FIG. 6, the AAP-values are in this pressure range "perinability-controlled".

For even higher pressures, larger than the gel blocking pressure Pgb, the permeability of the layer is approaching zero and the fluid can only be transported by diffusion resulting in very low AAP values. These very low values are not substantially additionally reduced with further increases in pressure.

Every hydrogel-forming material shows a characteristic pressure dependence of the AAP-values depicted in FIG. 6. The critical pressure is for example dependent on the gel properties ("gel stiffness") and the morphology of the materials. Stiffer materials are less deformable under pressure. They have therefore a higher Pcrit and a higher permeability. The AAP-value for pressures smaller than Pcrit is approaching the Teabag Centrifuge Capacity of the materials plus the added void spaces (determined via porosity).

Examples for Pcrit and Pgb for the materials referenced above are given in the table below.

| Pcrit [psi] | Pgb [psi] | Material | Comment |
|---|---|---|---|
| ~0 | <0.3 | IM 1000 | very weak gel |
| <0.3 | ~0.7 | SAB 990 | |
| >0.3 | >0.7 | SXM 50, SXM 100, W52859 | |
| >0.7 | >0.7 | W52521 | very strong gel, high GLP |

Considering the above mechanism for the pressure dependence of the AAP-values at the pressure Po, the effects of mixing two materials A and B are summarised in the table below. The mixing effect depends on the values of Pcrit and Pgb of each type of hydrogel-forming material. The AAP value of the mixture is determined at pressure Po.

| Material A | | Material B | | |
|---|---|---|---|---|
| Pcrit | Pgb | Pcrit | Pgb | Possible AAP Mixing Effect |
| >Po | >Po | >Po | >Po | mostly linear |
| >Po | >Po | <Po | >Po | 1. non-linear mixing Example: W52521/SXM 50 2. synergistic effect Example: W52521/W52859 |
| >Po | >Po | <Po | <Po | mostly non-linear, but could be completely gel blocked Example: W52521/IM 1000 |
| <Po | >Po | <Po | >Po | depends on exact properties, but can be non-linear Example: SXM 100/SAB 990 |
| >Po | >Po | <Po | >Po | synergistic effect Example: W52521/W52859 |
| >Po | >Po | <Po | >Po | synergistic effect |
| <Po | <Po | <Po | <Po | mostly linear (gel blocked) |

The reason for a non-linear mixing effect, or a synergistic effect, is that the stiffer material component can help increasing the permeability and therefore partially eliminate the limitations of the weaker material.

If both components, however, are not gel blocking limited, than the AAP values just mix according to a linear rule (weighted average).

The optimum mixing ratio for the materials depends on the detailed gel properties and on the particle size distribution.

It can easily be appreciated that all considerations are also applicable to mixtures of more than two components and that the inventions should not be understood as to be limited to binary mixtures.

The process of making a mixture according to the invention comprises mixing two particulate absobent gelling materials of different AAP- and/or TCC-values.

Figure 7:
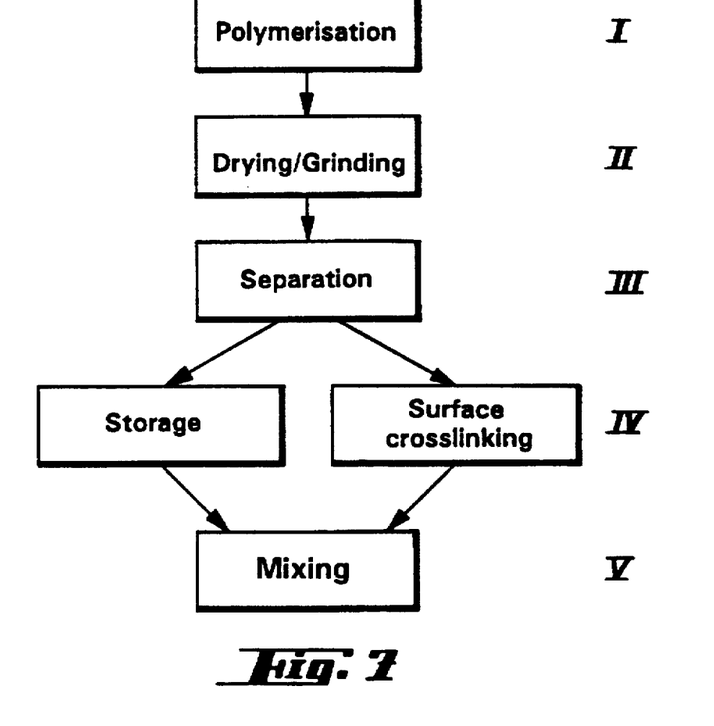

FIG. 7 schematically shows an embodiment of the process of manufacturing an absorbent material comprising a mixture of two types of hydrogel-forming particles.

In the first stage a bulk material is formed by polymerisation of precursor monomer material. Alternatively, a bulk material is supplied and is homogeneously crosslinked.

The second stage may comprise a drying step, in which the moisture content of the absorbent particles is fixed at between 5% and 20% by weight of the absorbent particles, preferably below 5%, and may comprise a grinding operation to obtain a predetermined particle size. The second step is optional and may be omitted if sufficiently dry particles of the required size are available.

The third step comprises a separation step, in this example a sieving step, to separate a fraction of the particle having a pre-determined particle size from the bulk material. In alternative embodiments the third step may comprise an electrostatic separation step, or an air separation step wherein lighter particles are deflected out of the main stream of bulk material by an air stream, a centrifuging step or a gravity separation.

In the fourth step, the separated fraction is surfaced crosslinked (e.g., by contacting with a surface-crosslinking agent and heating) and is in a fifth step mixed in its dry state, i.e. in its substantially unswollen ungelled state, with the main bulk fraction, using for instance Shugi mixers, Paddle mixers, air stream mixing or any equivalent method.

It is not absolutely necessary that the first two stages of polymerisation and drying are performed in the same process flow. It is of course possible to use readily made and commercially available bulk hydrogel- forming particles to stage 3.

Figure 8:
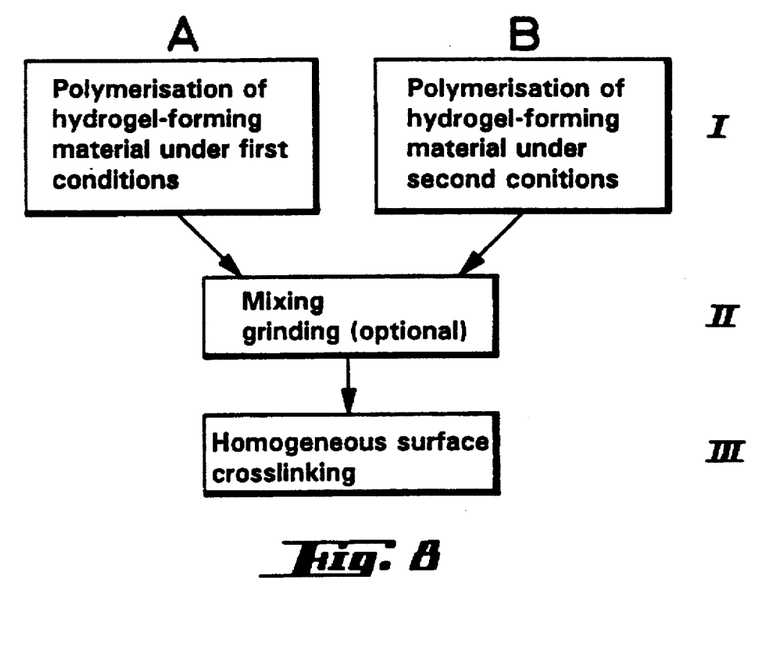

FIG. 8 shows an alternative method of manufacturing an absorbent material according to the invention. In the forming stage, two different reaction vessels A and B are used to provide different types of hydrogel-forming particles. These particles can be mixed in stage II and after mixing be surface crosslinked by application of a surface crosslinking agent in a third step.

The absorbent material according to the invention can be directly introduced into an absorbent product, the processes of FIG. 7 and 8 occurring on line. Alternatively, the mixture can be stored and or transported, and later used in the manufacturing of absorbent articles.

What is claimed is:

1. Absorbent gelling material comprising a dry mixture of at least a first hydrogel-forming particles and a second hydrogel forming particles,
   wherein the first hydrogel-forming particles has an Absorption Against Pressure value which is higher than the Absorption Against Pressure value of the second hydrogel-forming particles, the weight of the second hydrogel-forming particles forming at least 10% of the combined weight of the first and and second hydrogel-forming particles.

2. Absorbent gelling material according to claim 1, wherein the second hydrogel-forming particles have a mass median particle size not substantially smaller than the mass median particle size of the first hydrogel-forming particles.

3. Absorbent gelling material according to claim 1, wherein the difference in AAP-values of the first and the second material is at least 2 g/g.

4. Absorbent gelling material according to claims 1, wherein the first hydrogel-forming particles having an absorption against pressure value $AAP_1$, a fraction ,w, of the combined weight of the first and second hydrogel-forming particles is comprised of the first hydrogel-forming particles, a fraction p of the combined weight of the first and second hydrogel-forming particles being comprised of the second hydrogel-forming particles, than second hydrogel-forming particles having an absorption against pressure value $AAP_2$, wherein:

$$p+w=1,$$

and wherein for the absorption against pressure value of the mixture, $AAP_{1,2}$:

$$AAP_{1,2} > w \cdot AAP_1 + p \cdot AAP_2,$$

the absorption against pressure values being measured at pressures between 21.1 gcm$^{-2}$ (0.3 psi) and 70.3 gcm$^{-2}$ (1 psi), preferably between 35.2 gcm$^{-2}$ (0.5 psi) and 56.2 gcm$^{-2}$ (0.8 psi).

5. Absorbent gelling material according to claim 1, wherein at a pressure of 49.2 gcm$^{-2}$ (0.7 psi), the AAP-value of the first hydrogel-forming particles is at least 15 g/g.

6. Absorbent gelling material according to claim 1, wherein at a pressure of 49.2 gcm$^{-2}$ (0.7 psi), the AAP value of the second hydrogel-forming particles is not higher than 25 g/g.

7. Absorbent gelling material according to claim 1 wherein the AAP value of the first hydrogel-forming particles is at least 1.25 times higher than the AAP value of the second hydrogel-forming particles.

8. Absorbent gelling material comprising a dry mixture of at least a first hydrogel-forming particles and a second hydrogel-forming particles, characterised in that the first hydrogel-forming particles has a Teabag Centrifuge Capacity (TCC) value which is greater than the Teabag Centrifuge Capacity value of the second hydrogel-forming particles, the amount of the second hydrogel-forming particles forming at least 10% of the combined weight of the first and second hydrogel-forming-materials, the Absorption Against Pressure value of the mixture being higher than the Absorption Against Pressure value of either one of the first hydrogel-forming particles and the second hydrogel-forming particles, wherein the absorption against pressure values are measured at pressures between 21.1 gcm$^{-2}$ (0.3 psi) and 70.3 gcm$^{-2}$ (1 psi), preferably between 35.2 gcm$^{-2}$ (0.5 psi) and 56.2 gcm$^{-2}$ (0.8 psi).

9. Absorbent gelling material according to claim 8, characterised in that the Teabag Centrifuge Capacity value of the first hydrogel-forming material is at least 19 g/g.

10. Absorbent gelling material according to claims 8, wherein the Teabag Centrifuge Capacity value of the second hydrogel-forming material is not higher than 40 g/g.

11. Absorbent gelling material according to claim 8, wherein the amount of the second hydrogel forming particles is between 10% and 75% of the combined weight of the first and and second hydrogel-forming-materials, perferably between 20% and 60% of the combined weight of the first and second hydrogel-forming particles.

12. Absorbent gelling material according to claim 8, the mass median particle size of the first type of hydrogel-forming particles being between 50 and 400 micrometer, the mass median particle size of the second hydrogel-forming particles being between 250 and 800 micrometer.

13. Absorbent article comprising an absorbent gelling material according to claim 8.

14. Method of making an absorbent gelling material comprising a dry mixture of at least a first hydrogel-forming particles and a second type of hydrogel forming particles, the first hydrogel-forming particles having an Absorption Against Pressure value or a Teabag Centrifuge Capacity value which is higher than the Absorption Against Pressure value or the Teabag Centrifuge Capacity value of the second hydrogel-forming particles, the method comprising the steps of:

providing the first hydrogel-forming material and the second hydrogel-forming material;

introducing both hydrogel-forming material in a mixing means; and mixing both hydrogel-forming particles to form the mixture.

15. Method according to claim 14, charactericed in that the method comprises the steps of:

separating a fraction of hydrogel-forming particles from a bulk mass of hydrogel-forming particles, physically or chemically modifying the separated fraction of hydrogel-forming particles to increase the Absorption Against Pressure-value or the Teabag Centrifuge Capacity-value, or both, of the separated fraction to form the first hydrogel-forming particles; and mixing the modified separated fraction back into the bulk mass.

16. Method according to claim 15, wherein the separated fraction is obtained by sieving or air-separation, and wherein the separated fraction is modified by surface crosslinking.

17. Method of making an absorbent gelling material according to claim 14 characterised in that the method comprises the steps of:

polymerizing a first monomer forming the first hydrogel-forming particles polymerising a second monomer forming the second hgf-forming particles, and mixing the first type and second hydrogel-forming particles.

18. Method according to claim 17, wherein the first and second hydrogel-forming particles are surface cross-linked after having been mixed.

* * * * *

UNITED STATES PATENT AND TRADEMARK OFFICE
CERTIFICATE OF CORRECTION

PATENT NO.    : 5,714,156
DATED         : February 3, 1998
INVENTOR(S)   : Schmidt et al.

It is certified that error appears in the above-identified patent and that said Letters Patent is hereby corrected as shown below:

Column 4,
Line 38, after "g/g", please delete "," (the comma) and insert therefor -- . -- (a period).

Column 8,
Line 14, after "These", please delete "," (the comma).
Line 21, please delete "mothacrylic" and insert therefore -- methacrylic --.
Line 32, please delete "mothacrylic" and insert therefore -- methacrylic --.

Column 9,
Line 4, please delete "Dabmen" and insert therefor -- Dahmen --.

Column 11,
Line 65, please delete "g/cm$^{-31\ 2}$" and insert therefor -- gcm$^{-2}$ --.

Column 13,
Line 62, please delete "min." and insert therefor -- mm --.

Column 14,
Line 42, please delete "2 1" and insert therefor -- 21 --.

Column 17,
Line 24, after "g/g", please delete "," (the comma) and insert therefor -- . -- (a period).

Column 18,
Line 43, please delete "cortrolled" and insert therefor -- controlled --.
Line 53, please delete "perinability" and insert therefor -- "permeability --.

Column 19,
Line 50, please delete "inventions" and insert therefor -- invention --.

Column 20,
Line 41, please delete second occurrence of "and".
Line 50, please delete "claims" and insert therefor -- claim --.

UNITED STATES PATENT AND TRADEMARK OFFICE
CERTIFICATE OF CORRECTION

PATENT NO.    : 5,714,156
DATED         : February 3, 1998
INVENTOR(S)   : Schmidt et al.

It is certified that error appears in the above-identified patent and that said Letters Patent is hereby corrected as shown below:

Column 21,
Line 4, after "AAP" please delete "-" (the hyphen).
Lines 22 and 39, after "forming" please delete "-" (the hyphen).
Line 39, please delete second occurrence of "and".
Lines 39-40, please delete "prefer-ably" and insert therefor -- preferably --.
Line 43, after "first", please delete "type of".

Column 22,
Line 5, after "second", please delete "type of".
Line 18, please delete "charactericed" and insert therefor -- characterised --.
Line 24, after "Pressure", please delete "-" (the hyphen).
Line 25, after "Capacity", please delete "-" (the hyphen).
Line 37, please delete "polymerising" and insert therefor -- polymerizing --.

Signed and Sealed this

Eleventh Day of February, 2003

JAMES E. ROGAN
*Director of the United States Patent and Trademark Office*